United States Patent [19]

Subramanian

[11] 4,422,982

[45] Dec. 27, 1983

[54] METHOD FOR PREPARATION OF N-PHOSPHONOMETHYLGLYCINE

[75] Inventor: N. Subramanian, San Leandro, Calif.

[73] Assignee: Stauffer Chemical Company, Westport, Conn.

[21] Appl. No.: 393,574

[22] Filed: Jun. 30, 1982

[51] Int. Cl.³ .............................................. C07F 9/38
[52] U.S. Cl. ............................................. 260/502.5 F
[58] Field of Search .................... 260/502.5 F, 502.5 E

[56] References Cited

U.S. PATENT DOCUMENTS

| | | | |
|---|---|---|---|
| 4,009,204 | 2/1977 | Krueger et al. | 260/502.5 E |
| 4,053,505 | 10/1977 | Dutra | 260/502.5 F |
| 4,237,065 | 12/1980 | Ehrat | 260/502.5 F |

OTHER PUBLICATIONS

Wagner et al, "Synthetic Organic Chemistry", (1953), pp. 678, 679.

*Primary Examiner*—J. E. Evans
*Attorney, Agent, or Firm*—Paul R. Martin

[57] ABSTRACT

A method for the production of N-phosphonomethylglycine is disclosed which comprises the steps of:
 (a) reacting formaldehyde with formamide at a pH of 9–10 to form N-(hydroxymethyl)formamide,
 (b) reacting N-(hydroxymethylformamide with triethylphosphite to form diethyl, N-(formyl)aminomethylphosphonate,
 (c) reacting diethyl, N-(formyl)aminomethylphosphonate with methylchloroacetate to form N-(diethylphosphonomethyl), N-(formyl)glycinemethyl ester, and
 (d) reacting N-(diethylphosphonomethyl), N-(formyl)glycinemethyl ester with hydrochloric acid to form N-phosphonomethylglycine.

11 Claims, No Drawings

METHOD FOR PREPARATION OF N-PHOSPHONOMETHYLGLYCINE

BACKGROUND OF THE INVENTION

This invention relates to a novel method for the preparation of N-phosphonomethylglycine, a compound which is a known herbicide and plant growth regulator.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are normally incorporated into the soil prior to the emergence of the weed plants from the soil, and the post-emergence herbicides are normally applied to plant surfaces after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxy acetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have been made to develop herbicides which are biodegradable into harmless residues within a relatively short time after their application.

One such compound, which has been found to be biodegradable, yet which is effective as a herbicide and plant growth regulator when employed at lower rates, is N-phosphonomethylglycine and various salts thereof. The N-phosphonomethylglycine and agriculturally effective salts have been approved for use by the U.S. Government, and, as a consequence, this herbicide has become extremely successful commercially.

The N-phosphonomethylglycine and certain salts are the only effective and approved post-emergence herbicides in the field. The present commercial compound is the isopropylamine salt of N-phosphonomethylglycine and derivatives thereof.

In field use it is normally applied in amounts of from 0.01 to about 20 pounds per acre, preferably from 2 to 6 pounds per acre.

The N-phosphonomethylglycines, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reaction products. Other methods include the phosphonomethylation of glycine and the reaction of ethyl glycinate with formaldehyde and diethylphosphite. The latter method is described in U.S. Pat. No. 3,799,758 (Franz, Mar. 26, 1974). In addition, there is a whole series of patents, relating to N-phosphonomethylglycines, their salts, and derivatives thereof, described as being useful herbicides and plant growth regulators. Such additional patents relating to the N-phosphonomethylglycines, methods of application, methods of preparation, salts, and derivatives, include U.S. Pat. Nos. 3,868,407, 4,197,254, and 4,199,354, among others.

Because of the importance of N-phosphonomethylglycine and certain salts as a herbicide, other methods of making the compounds are constantly being sought in order to provide improved or alternate methods of manufacture.

The instant invention is thus concerned with a novel method for the production of N-phosphonomethylglycine and specific intermediates.

DESCRIPTION OF THE INVENTION

The present invention is a process for the preparation of N-phosphonomethylglycine utilizing formaldehyde and formamide as starting materials and which in toto comprises four steps. Some of these steps are specific to certain compounds, and others are generic in nature. For that reason, the invention as a whole will be first described with regard to the specific compounds, and then each of the steps will be treated separately in substantial detail and the generic aspects, where applicable, will be described.

Thus, the overall process of this invention comprises the following steps:

(1) addition reaction of formaldehyde to formamide while maintaining the reaction solution at a pH of between 9 and 10, to form N-(hydroxymethyl)formamide, (2) reaction of N-(hydroxymethyl)formamide with triethylphosphite with accompanying heat, to form diethyl-N-(formyl)aminomethylphosphonate, (3) reaction of diethyl-N-(formyl)aminomethylphosphonate with methylchloroacetate in the presence of a suitable solvent to form N-(diethylphosphonylmethyl)-N-(formyl)glycinemethyl ester, and (4) reaction of N-(diethylphosphonomethyl)-N-(formyl)glycinemethyl ester with a suitable hydrolyzing agent to form N-phosphonomethylglycine.

The invention will now be discussed on a step by step basis.

According to the prior art literature, N-(hydroxymethyl) formamide can be prepared simply by combining formamide and formaldehyde with heating. When this reaction is carried out in a laboratory, the product obtained is N-bishydroxymethyl formamide, which has the structure:

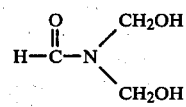

This structure can be confirmed by $^{13}C$ nuclear magnetic resonance. This is not the desired intermediate product for use in the process of the invention.

Step 1

It has now been discovered that the desired intermediate product, N-(hydroxymethyl)formamide, can be prepared by inverse addition of formaldehyde to formamide at room temperature while maintaining the pH of the reaction solution between 9 and 10. This reaction can be represented as follows, and represents the first step of the process of the invention.

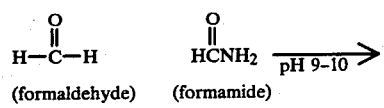 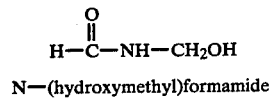 (1.)

(formaldehyde)   (formamide)

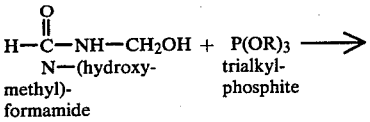

N—(hydroxymethyl)formamide

In the reaction set forth above, step (1), one equivalent of formaldehyde is used for every two equivalents of formamide. The pH of the reaction solution is critical, and must be maintained at between about 9 and 10. The pH can be adjusted by any suitable means, however, it is preferred to use bases such as potassium carbonate, sodium carbonate, sodium bicarbonate, sodium hydroxide and potassium hydroxide, with the most preferred base being potassium carbonate.

In the process as described in step (1), the formaldehyde must be added to the formamide, because it has been found that this is the only way that the desired product, N-(hydroxymethyl)formamide, can be obtained. If the formamide is added to the formaldehyde, the desired end product is not achieved.

The reaction can be conducted at room temperature, and in that instance, the reaction time is about 4 hours. If heat is used, then of course, the reaction time will be substantially reduced. The use of heat is not essential, however. Desirably, the temperature of the reaction solution will range from about 20° to 25° C.

Step 2

The N-(hydroxymethyl)formamide is next reacted with a triethylphosphite compound to form diethyl-N-(formyl)-aminomethylphosphonate. This reaction can be represented as follows:

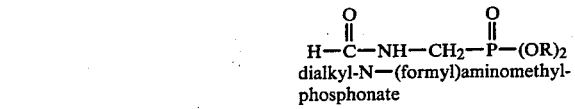 (2a)

N—(hydroxymethyl)-formamide   triethylphosphite

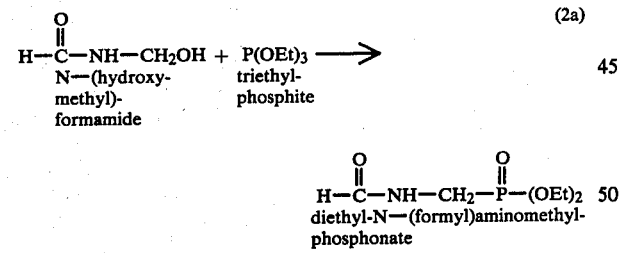 50 diethyl-N—(formyl)aminomethylphosphonate

The mole ratio of N-(hydroxymethyl)formamide to triethylphosphite in step (2) of the process of the invention is 1:1. The reaction is conducted in the presence of heat and at a temperature sufficient to cause the reaction to go to completion. The reactants are heated until ethyl alcohol starts to evolve and this occurs at reflux temperature. When triethylphosphite is used, this temperature is approximately 120°–125° C. At this point, the alcohol is distilled off, leaving the product diethyl-N-(formyl)aminomethylphosphonate as the residue.

The process of step (2) as set forth, can also be considered to be a generic process in which the N-(hydroxymethyl)-formamide is reacted with a trialkylphosphite of the formula P(OR)₃, wherein R is an alkyl radical having from 1–6 carbon atoms, to produce a dialkyl-N-(formyl)aminoethylphosphonate. In a generic sense, therefore, this reaction can be represented as follows:

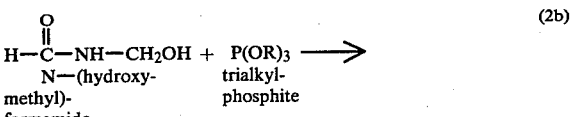 (2b)

N—(hydroxymethyl)-formamide   trialkylphosphite

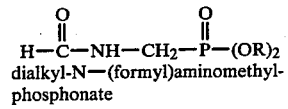

dialkyl-N—(formyl)aminomethylphosphonate

The conditions of the reaction when a trialkylphosphite is used instead of triethylphosphite are in general the same as the conditions when triethylphosphite is the compound of choice, i.e., the ratio of N-(hydroxymethyl)formamide to trialkylphosphite is still 1:1, and the reaction is conducted in the presence of heat and at a temperature sufficient to cause the reaction to go to completion. In general, the temperature will range from about 80° to 150° C., and the time will range from about 2 to about 3 hours, but the exact temperature and time of the reaction will depend upon the specific nature of the trialkylphosphite compound used. Suitable trialkylphosphites for use in the invention include triethylphosphite, tripropylphosphite, tributylphosphite and others of a like nature.

Step 3

The process in the third step of the process of the invention comprises reacting diethyl-N-(formyl)aminomethylphosphonate with methylchloroacetate in the presence of a proton-extracting base and a suitable solvent to produce N-(diethylphosphonomethyl)-N-(formyl)glycine methyl ester.

This reaction, in a limited sense, can be represented as follows:

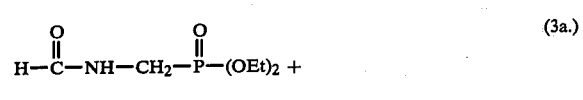 (3a.)

diethyl-N—(formyl)-aminomethyl phosphonate

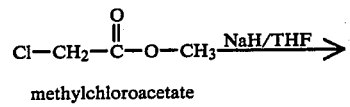

methylchloroacetate

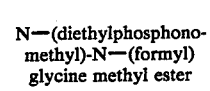

N—(diethylphosphonomethyl)-N—(formyl) glycine methyl ester

This reaction, in a generic sense, can be represented as follows:

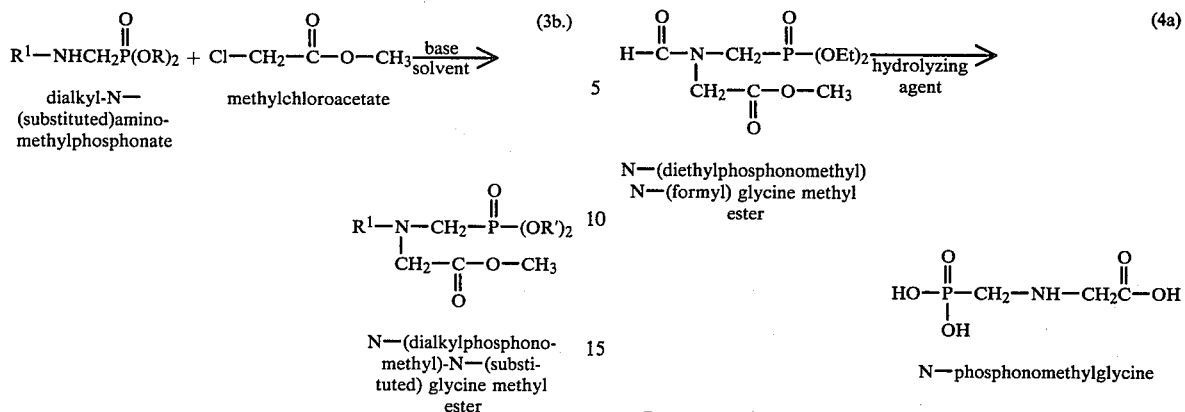

In the formula set forth in 3b above, $R^1$ is a radical selected from group consisting of formyl, acetyl, methoxycarbonyl, phenyloxycarbonyl, and benzyl, and R is a radical selected from the group consisting of methyl, ethyl, propyl, butyl, pentyl, and hexyl.

The reaction of steps (3a) or (3b) above are carried out in the presence of a suitable solvent, and suitable solvents include tetrahydrofuran, toluene, methylisobutylketone, dimethylformamide, or any other organic solvent of a similar nature.

It is essential that the reaction also be carried out in the presence of a proton-extracting base, and suitable bases include sodium hydride and potassium carbonate. The preferred base for use is sodium hydride.

The preferred solvent for use in the process described in step (3) above is tetrahydrofuran.

The mole ratio of dialkyl-N-(substituted)aminomethylphosphonate to methylchloroacetate used in the process of step (3) is 1:1.

The process is conducted at a sufficient temperature and for a sufficient time for the reaction to go to completion. The exact time will vary depending, of course, upon the nature of the starting compound used, however, when diethyl-N-(formyl)aminomethylphosphonate is the starting compound, then the reaction is preferably conducted at a temperature ranging from about 10° to 25° C. for about 2 hours.

Preferred starting compounds for the reaction set forth in step (3) above include diethyl-N-(formyl)aminomethylphosphonate.

The preferred compounds for use in step (3) of the process of the invention include diethyl-N-(formyl)aminomethylphosphonate, methylchloroacetate, and tetrahydrofuran as a solvent, plus sodium hydride as the proton-extracting base.

Step 4

The process of the invention comprises reaction of N-(diethylphosphonomethyl), N-(substituted)glycinemethyl ester with a hydrolyzing agent to form the desired end product, N-phosphonomethylglycine. The starting compound in step (4) of the reaction is the product achieved in step (3), and the preferred starting compound is thus N-(diethylphosphonomethyl), N-(formyl)glycinemethyl ester.

This reaction can be represented as follows:

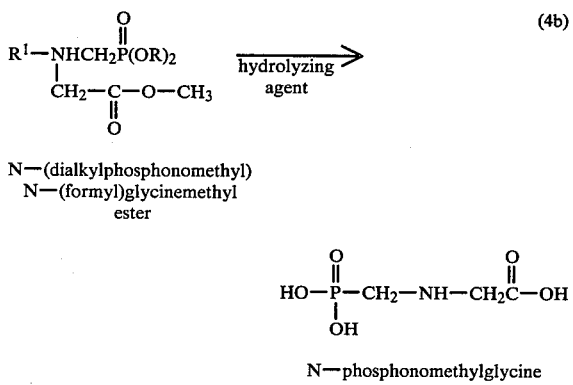

In a generic sense, the reaction can be stated as follows:

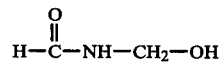

wherein R and $R^1$ are the same as in step 3.

Any hydrolyzing agent can be used in step (4) of the reaction, however, hydrochloric acid is the preferred hydrolyzing agent. Other suitable hydrolyzing agents include hydrobromic acid and sulfuric acid, for example. The N-phosphonomethylglycine produced in accordance with the method of step (4) can be separated from the reactants by any suitable means, including filtration of the precipitate.

The preferred reactants of step (4) are N-(diethylphosphonomethyl), N-(formyl)glycinemethyl ester and hydrochloric acid as the hydrolyzing agent. The hydrolyzing agent is preferably used in excess.

When the preferred compounds are used, the reaction is preferably conducted at a temperature ranging from about 120° to 125° C.

This invention will be more readily understood by reference to the following examples which are intended to be illustrative of the invention but not limiting in any way.

EXAMPLE I

Preparation of N-(hydroxymethyl)formamide

N-(hydroxymethyl)formamide has the structure:

$$H-\overset{O}{\overset{\|}{C}}-NH-CH_2-OH$$

It can be prepared in the laboratory by the dropwise addition of 1 part 41% formaldehyde to 2 parts formamide. This reaction may be carried out as follows:

Two grams (g) of anhydrous potassium carbonate were added to 32.4 g of 41% formaldehyde. This formaldehyde/potassium carbonate solution was then added dropwise to 40.0 g of 98% formamide at room temperature and then stirred for 1 hour. The resulting solution was stripped, washed once with acetone and methanol, dried over sodium sulfate, filtered and stripped again. The product obtained was 51.3 g of a clear liquid. $^{13}C$ NMR supported the proposed structure: N-(hydroxymethyl)formamide. ($^{13}C$ NMR is Carbon 13 nuclear magnetic resonance).

The N-(hydroxymethyl)formamide prepared in Example I can be used to synthesize diethyl, N-(formyl)aminomethylphosphonate by the procedure described in Example II.

EXAMPLE II

Preparation of Diethyl-N-(formyl)aminomethylphosphonate

Thirty and nine-tenths milliliters (ml) of triethyl phosphite were added dropwise to 22.5 g of N-(hydroxymethyl)formamide in a reaction flask. Room temperature was maintained during the addition. The reaction mixture was heated to reflux and ethanol and the excess triethyl phosphite were distilled off. The resulting material was 30.0 g of a clear orange liquid hypothesized to be about 54% diethyl, N-(formyl)aminomethylphosphonate. $^{13}$NMR, IR and proton IMR supported the proposed structure.

The diethyl, N-(formyl)aminomethylphosphonate can be alkylated to give N-(diethylphosphonomethyl), N-(formyl)glycinemethyl ester as described in Example III.

EXAMPLE III

Preparation of N-(diethylphosphonomethyl), N-(formyl)glycinemethyl ester

To 0.32 g (0.0132 mole) of dry sodium hydride taken in 10 ml of tetrahydrofuran was added 2.35 g of diethyl N-(formyl)aminomethyl phosphonate in 10 ml tetrahydrofuran and then stirred at room temperature under $N_2$ for 30 minutes. To the clear solution obtained was added 1.3 g (0.012 mole) of methylchloroacetate and stirred at ambient temperature for 12 hours.

The product obtained was a cloudy yellow solution which was filtered through celite, washed with tetrahydrofuran and then stripped at 40° C. with high vacuum. The resulting product was 2.34 g of a cloudy yellow solution. Structure was confirmed as N-(diethylphosphonomethyl)-N-(formyl)glycinemethyl ester by GC and MS. (GC is gas chromatography; MS is mass spectroscopy).

The N-(diethylphosphonomethyl) N-(formyl)glycinemethyl ester prepared in Example III can be hydrolyzed to give N-phosphonomethylglycine as described in Example IV.

EXAMPLE IV

Preparation of N-phosphonomethylglycine

Nine-tenths g of N-(diethylphosphonomethyl), N-(formyl)glycinemethyl ester and 20 ml of concentrated hydrochloric acid were taken in a reaction flask and refluxed for 16 hours. The solution was stripped to dryness and 2.3 ml of ethanol was added. A precipitate formed and was filtered. Product obtained was 400 mg of a white solid which was hypothesized to be N-phosphonomethylglycine. Structure was confirmed by high pressure liquid chromatography, nmr, and $^{13}C$ nmr.

The N-phosphonomethylglycine compounds which are produced in accordance with the method of the invention, in and of themselves, have herbicidal and plant growth regulating efficacy. However, because the acid form is not in itself very soluble in aqueous solutions, it is preferred to convert these compounds to their salt forms for inclusion into herbicidal compositions. Salt forms which have been found to have high rates of herbicidal activity and plant growth regulating activity are the trialkylsulfonium salts of N-phosphonomethylglycine, such as are disclosed in U.S. Pat. No. 4,315,765. Methods of preparation for N-phosphonomethylglycine are described in that patent.

What is claimed is:

1. A method for the production of N-phosphonomethylglycine which comprises the steps of:
    (a) adding about one mole of formaldehyde to about two moles of formamide at a pH of between 9 and 10, to form N-(hydroxymethyl)formamide,
    (b) reacting N-(hydroxymethyl)formamide with triethyl phosphite in about a 1:1 mole ratio to form diethyl, N-(formyl)aminomethylphosphonate,
    (c) reacting diethyl, N-(formyl)aminomethylphosphonate with methylchloroacetate in about a 1:1 mole ratio in the presence of a suitable solvent and a proton-extracting base to form N-(diethylphosphonomethyl), N-(formyl)glycine-methyl ester, and
    (d) reacting N-(diethylphosphonomethyl) N-(formyl)glycine methyl ester with a hydrolyzing agent to form N-phosphonomethylglycine.

2. The method of claim 1 in which step (a) is conducted at a temperature ranging from about 20° to about 25° C., and for a period of time sufficient to cause completion of the reaction.

3. The method of claim 1 in which step (b) is conducted at a temperature ranging from about 120° to about 125° C. and for a period of time sufficient to cause completion of the reaction.

4. The method of claim 1 in which reaction step (c) is conducted in the presence of sodium hydride as a proton-extracting base and tetrahydrofuran as a solvent wherein said reaction is conducted at a temperature ranging from about 10° to about 25° C.

5. The method of claim 1 in which step (d) is conducted at a temperature ranging from about 120° to about 125° C., wherein the mole ratio of N-(diethylphosphonomethyl), N-(formyl)glycinemethyl ester to hydrochloric acid ranges from about 1 to about 5.

6. The method of claim 1 in which the solvent used in step (c) is selected from the group consisting of tetrahydrofuran toluene, dimethylformamide and xylene.

7. The method of claim 1 in which the hydrolyzing agent of step (d) is hydrochloric acid.

8. A method for the production of N-phosphonomethylglycinne which comprises the steps of:
    (a) reacting an aminomethylphosphonate compound of the formula

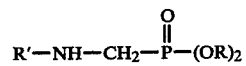

wherein
R′ is selected from the group consisting of formyl, acetyl, methoxycarbonyl, phenyloxycarbonyl, and benzyl, and R is selected from the group consisting of methyl, ethyl, propyl, butyl, pentyl and hexyl with methylchloroacetate in the presence of an organic solvent, and a proton-extracting base at such temperature to cause the reaction to go to completion to form as an intermediate product, N-(dialkylphosphonomethyl), N-(substituted)glycinemethyl ester, and (b) reacting said N-(dialkylphosphonomethyl), N-(substituted)glycinemethyl ester with a hydrolyzing agent at a sufficient temperature and for a sufficient time to cause formation of N-phosphonomethylglycine.

9. The method of claim 8 in which said solvent is selected from the group consisting of tetrahydrofuran, toluene, methylisobutylketone, and dimethylformamide.

10. The method of claim 8 in which said proton-extracting base is sodium hydride.

11. The method of claim 8 in which said hydrolyzing agent is hydrochloric acid.

* * * * *